United States Patent [19]

Jarrett et al.

[11] 4,117,112

[45] Sep. 26, 1978

[54] VACCINE FOR PREVENTION OF FELINE LEUKEMIA

[75] Inventors: William Fleming Hoggan Jarrett; James Oswald Jarrett; Lindsay Joan Mackey, all of Glasgow, Scotland

[73] Assignee: University of Glasgow, Glasgow, Scotland

[21] Appl. No.: 798,509

[22] Filed: May 19, 1977

Related U.S. Application Data

[60] Continuation-in-part of Ser. No. 668,110, Mar. 18, 1976, Pat. No. 4,034,081, which is a division of Ser. No. 505,625, Sep. 13, 1974, Pat. No. 3,966,907.

[30] Foreign Application Priority Data

Sep. 18, 1973 [GB] United Kingdom ............... 43642/73

[51] Int. Cl.$^2$ ............................................. A61K 39/12
[52] U.S. Cl. ...................................................... 424/89
[58] Field of Search ............................................ 424/89

[56] References Cited

U.S. PATENT DOCUMENTS

| 3,966,907 | 6/1976 | Jarrett et al. | 424/89 |
| 4,034,081 | 7/1977 | Jarrett et al. | 424/89 |

OTHER PUBLICATIONS

Jarrett et al., Int. J. Cancer 16:134–141, (1975) "Vaccination Against Feline Leukemia Using a Cell Membrane Antigen System".

*Primary Examiner*—Shep K. Rose
*Attorney, Agent, or Firm*—John J. McDonnell

[57] ABSTRACT

The present invention encompasses a vaccine for the prevention of disease associated with feline leukemia virus which comprises an effective amount of an adjuvant and about $10^5$–$10^7$ feline lymphoblastoid cells chronically infected with feline leukemia virus and having viral associated antigen on their surface wherein the virus and cells are inactivated by chemical or physical means without destroying immunogenicity.

7 Claims, No Drawings

VACCINE FOR PREVENTION OF FELINE LEUKEMIA

This is a continuation-in-part of U.S. patent application Ser. No. 668,110, filed Mar. 18, 1976, now U.S. Pat. No. 4,034,081, which is a divison of U.S. patent application Ser. No. 505,625, filed Sept. 13, 1974, now U.S. Pat. No. 3,966,907.

The present invention encompasses a vaccine for the prevention of disease associated with feline leukemia virus which comprises an effective amount of an adjuvant and about $10^5$–$10^7$ feline lymphoblastoid cells chronically infected with feline leukemia virus and having viral associated antigen on their surface wherein the virus and cells are inactivated by chemical or physical means without destroying immunogenicity. Unexpectedly, the adjuvant makes the killed vaccine almost as effective as the live vaccine.

A preferred embodiment is a vaccine for the prevention of disease associated with feline leukemia virus which comprises an effective amount of aluminum hydroxide as adjuvant and about $10^5$–$10^7$ feline lymphoblastoid cells chronically infected with feline leukemia virus and having viral associated antigen on their surface wherein the virus and cells are inactivated by chemical or physical means without destroying immunogenicity. Economically $10^5$–$10^6$ cells are preferred.

A most preferred embodiment is a vaccine for the prevention of disease associated with feline leukemia virus which comprises an effective amount of aluminum hydroxide as adjuvant and at least $1 \times 10^6$ FL 74 cells inactivated with paraformaldehyde.

Cells useful for the vaccines are feline lymphoblastoid cells chronically infected with feline leukemia virus. FL 74 cells which were developed from feline leukemia virus-induced lymphoma, Theilen et al. Nature 272 589–590 and which are commonly used as a target cell in the indirect membrane fluorescent test, Essex et al. Intern. J. Cancer 8, 384–390, 1971. These cells are further described in Cancer Research 36, 3642–3646, 1976.

Adjuvants such as Freund's complete or incomplete adjuvant, killed hemophilus pertussis, synthetic adjuvants and analogs described in Rowe, Natl. Acad. Sci. 73, 2472–2475 (1976), kaolin, charcoal, lanolin, tapioca, solid paraffin, paraffin oil, light mineral oil, phosphorylated hespiridin magnesium salts, calcium salts, and staphylococcal toxoid are useful.

Particularly useful are aluminum hydroxide gels which are 0.1–10% aluminum hydroxide. For example, 0.5 ml of 2% aluminum hydroxide in combination with 0.5 ml of media containing FL 74 cells ($1 \times 10^5$, $1 \times 10^7$) provides a preferred vaccine. Thus, about 1% of aluminum hydroxide is desirable.

The cells and virus are inactivated by chemical or physical means so as not to destroy the immunogenicity. Thus, thermal (Cancer Research 36 3642–3646, 1976), ultrasonication, γ-irradiation at about 2.5 megarads are suitable physical means of inactivating the cells and the virus without destroying immunogenicity.

Chemical inactivation by conventional means are particularly effective and inactivation with 0.05–5% paraformaldehyde solution is preferred. In a most preferred method 2 grams of paraformaldehyde is added to 20 ml of distilled water and heated to 60° C. Then 0.1% normal sodium hydroxide is added dropwise until the solution clarifies. 30 ml of 0.25 molar phosphate buffer pH 7.2 and 425 mg of sodium chloride are added. The solution is filtered and stored at −20° C. in 20 ml aliquots. This solution is diluted before use with phosphate buffered saline to give a 0.1% solution and when mixed with the cell suspension give a final concentration of 0.05% paraformaldehyde.

Vaccines of the present invention are preferably administered in a single dose to young cats but multiple doses are also acceptable. Vaccines of the present invention protect cats from cat to cat transmission of FeLV and the resulting diseases.

Thus, $10^5$–$10^7$ feline lymphoblastoid cell chronically infected with feline leukemia virus have sufficient antigen to provoke in the presence of adjuvant a FOCMA antibody response (i.e. a titre of about 100) to provide protection against virulent feline leukemia virus. Therefore, the cells may be fragmented and the membrane fragments isolated and combined with an adjuvant to provide a vaccine which comprises FOCMA containing cell membrane fragments from $10^5$–$10^7$ feline lymphoblastoid cells chronically infected with feline leukemia virus wherein the virus and cells are killed by chemical or physical means without destroying immunogenicity. The use of FL 74 cells and the previously described aluminum hydroxide gels as adjuvant are preferred.

In a similar manner crude FOCMA extracts are isolated from $10^5$–$10^7$ feline lymphoblastoid cells chronically infected with feline leukemia virus, preferably from FL 74 cells by conventional protein isolation techniques and combined in a pharmaceutically acceptable carrier together with an effective amount of an adjuvant, preferably aluminum hydroxide gel. As before, the cells and virus are killed by chemical or physical means without destruction of immunogenicity.

The hereinafter set forth examples are intended to illustrate the present invention and are not intended to limit the invention in spirit or scope.

EXAMPLE 1

The following procedure is carried out at +4° C. Antigen bearing lymphoblast (FL 74 cells) on the second day of their growth cycle are pelleted and resuspended in cold phosphate buffered saline (PBS). They are washed three times for 2 minutes, resuspended and pelleted at 1500 rpm. The cells are suspended in PBS and an equal volume of 0.1% paraformaldehyde solution is added drop-wise as the suspension is being continuously mixed. This suspension is allowed to stand at +4° C. for 24 hours. The cells are pelleted at 2000 rpm for 10 minutes in a refrigerated centrifuge at +4° C. The paraformaldehyde solution is removed and the cells are washed 3 times with cold PBS to give aliquots of 1 ml containing the desired number of cells per dose.

The above paraformaldehyde solution is prepared by adding 2 grams of paraformaldehyde to 20 ml of distilled water and heating to 60° C. until dissolution. 0.1 N sodium hydroxide is added drop by drop until the solution clears at which time heat is removed. 30 Ml of 0.25 molar phosphate buffer pH 7.2 and 425 mg of sodium chloride are then added. The solution is filtered and stored at −20° C. in 20 ml aliquots and this solution is further diluted with PBS to provide a 0.1% by weight paraformaldehyde solution and when mixed with cells the concentration is 0.05% by weight.

Aluminum hydroxide adjuvanted vaccines are prepared by combining 0.5 ml of the desired number of cells and 0.5 ml of 2% aluminum hydroxide gel:

| 0.5 ml | 0.5 ml containing |
| --- | --- |
| 2% Al(OH)$_3$ | 1 × 10$^5$ cells |
| 2% Al(OH)$_2$ | 5 × 10$^5$ |
| 2% Al(OH)$_3$ | 1 × 10$^6$ |
| 2% Al(OH)$_3$ | 2 × 10$^6$ |
| 2% Al(OH)$_3$ | 5 × 10$^6$ |
| 2% Al(OH)$_3$ | 1 × 10$^7$ |
| 2% Al(OH)$_3$ | 2 × 10$^7$ |
| 2% Al(OH)$_3$ | 5 × 10$^7$ |

EXAMPLE 2

Groups of 6 cats were treated with vaccines consisting of 2 × 10$^7$ live cells, 2 × 10$^7$ paraformaldehyde inactivated cells, 2 × 10$^7$ paraformaldehyde cells adjuvantted with 2% aluminum hydroxide and 2 control groups of six cats each were also maintained. Pre-inoculation serum samples were taken from all cats and were examined for the presence of feline leukemia virus (FeLV), feline oncornovirus-associated cell membrane antigen (FOCMA) antibodies and neutralizing antibodies; all were negative in all of the tests. The animals were bled six weeks after vaccination. The mean titres for FOCMA antibodies:

| | FOCMA |
| --- | --- |
| Live cell group | 256 |
| Paraformaldehyde treated cells | 4 (3 animals responded 3 were negative) |
| Paraformaldehyde + 2% Al(OH)$_3$ | 100 |

Four animals in the live vaccination group had minimal (i.e. titres of 4) neutralizing titres while no other animals showed any. All groups were negative for virus isolation.

Each cat in the vaccinated groups and six of the 12 control animals were then challenged with 2 × 10$^6$ infectious units of a known potent leukaemogenic strain of FeLV.

One month after challenge, the FOCMA titre of the live vaccine group was 256; the paraformaldehyde group was 8 (four responded and two did not); and for the paraformaldehyde plus aluminum hydroxide group was 200. The challenge controls had FOCMA titre of 2 (one responded and five did not) and the uninfected controls remained negative throughout for all parameters. The animals were all post mortemed 6 weeks after challenge and virus isolation was carried out. All of the cats in the live vaccine group were negative for FeLV, three of six were positive in the paraformaldehyde group and one of six was positive in the aluminum hydroxide adjuvanted group. All of the challenge controls were positive.

This experiment demonstrates that an adjuvanted killed cell vaccine can produce FOCMA titres almost as high as the live cell vaccine in a short period of time and that these animals are resistant to a very high challenge. The vaccine was completely sterile and no viraemia was produced in the vaccinated cats.

EXAMPLE 3

Four groups, each of 10 cats, were injected intramuscularly with a range of doses of paraformaldehyde treated FL 74 cells plus 2% Al (OH)$_3$ adjuvant as in the last experiment, to determine the smallest number of cells which would give an effective FOCMA antibody response. In addition, this vaccine has been stored for 6 months at −70° C. before use. 15 Young adult cats were used as challenge controls. After 5 weeks all cats were injected with potant FeLV and were bled for plasma, virus and serum samples every fortnight. Mouth swabs were taken at these times.

The cell doses were 1 × 10$^6$, 5 × 10$^6$, 1 × 10$^7$ and 2 × 10$^7$. The respective FOCMA titres reached one month after vaccination in these groups were 100, 120, 128 and 256. The vaccines were all sterile and no cat developed any ciraemia. All of these titres are regarded as being within the normal range for protection.

What is claimed is:

1. A vaccine for the prevention of disease associated with feline leukemia virus which comprises an effective amount of adjuvant and about 10$^5$–10$^7$ feline lymphoblastoid cells chronically infected with feline leukemia virus and having viral associated antigen on their surface wherein the virus and cells are inactivated by chemical or physical means without destroying immunogenicity.

2. A vaccine for the prevention of disease associated with feline leukemia virus which comprises an effective amount of aluminum hydroxide as adjuvant and about 10$^5$–10$^7$ feline lymphoblastoid cells chronically infected with feline leukemia virus and having viral associated antigen on their surface wherein the virus and cells are inactivated by chemical or physical means with destroying immunogenicity.

3. A vaccine for the prevention of disease associated with feline leukemia virus which comprises an effective amount of aluminum hydroxide as adjuvant and about 1 × 10$^6$ FL 74 cells inactivated with paraformaldehyde.

4. A vaccine for the prevention of disease associated with feline leukemia virus which comprises an effective amount of adjuvant and FOCMA containing cell membrane fragments from 10$^5$–10$^7$ feline lymphoblastoid cells chronically infected with feline leukemia virus wherein the virus and cells are inactivated by chemical or physical means without destroying immunogenicity.

5. A vaccine according to claim 4 wherein the cells are paraformaldehyde killed FL 74 cells and the adjuvant is aluminum hydroxide.

6. A vaccine for the prevention of disease associated with feline leukemia virus which comprises an effective amount of adjuvant and crude FOCMA extracts from 10$^5$–10$^7$ feline lymphoblastoid cells chronically infected with feline leukemia virus wherein the virus and cells are inactivated by chemical or physical means without destroying immunogenicity.

7. A vaccine according to claim 6 wherein the cells are paraformaldehyde killed FL 74 cells and the adjuvant is aluminum hydroxide.

* * * * *